United States Patent
Butz et al.

(10) Patent No.: US 8,828,039 B2
(45) Date of Patent: Sep. 9, 2014

(54) PRICKING DEVICE FOR TAKING A BLOOD SAMPLE

(75) Inventors: Marion Butz, Regensburg (DE); Andreas Knie, Regensburg (DE); Vojan Vaclav, Pizen (CZ)

(73) Assignee: Gerresheimer Regensburg GmbH, Regensburg (DE)

( * ) Notice: Subject to any disclaimer, the term of this patent is extended or adjusted under 35 U.S.C. 154(b) by 317 days.

(21) Appl. No.: 12/996,218

(22) PCT Filed: May 29, 2009

(86) PCT No.: PCT/EP2009/056597
§ 371 (c)(1),
(2), (4) Date: Feb. 16, 2011

(87) PCT Pub. No.: WO2009/147082
PCT Pub. Date: Dec. 10, 2009

(65) Prior Publication Data
US 2011/0144683 A1    Jun. 16, 2011

(30) Foreign Application Priority Data

Jun. 6, 2008   (DE) .......................... 10 2008 027 272
Aug. 8, 2008   (DE) .......................... 10 2008 037 082

(51) Int. Cl.
| A61B 17/14 | (2006.01) |
| A61B 17/32 | (2006.01) |
| A61B 5/155 | (2006.01) |
| A61B 5/15  | (2006.01) |

(52) U.S. Cl.
CPC .............. *A61B 5/1411* (2013.01); *A61B 5/1427* (2013.01)

USPC ......................................................... 606/182

(58) Field of Classification Search
USPC ........................... 606/167, 171, 181, 182, 185
See application file for complete search history.

(56) References Cited

U.S. PATENT DOCUMENTS

| 4,643,189 A | 2/1987 | Mintz |
| 5,196,025 A * | 3/1993 | Ranalletta et al. ............ 606/182 |

(Continued)

FOREIGN PATENT DOCUMENTS

| DE | 19909602 A1 | 9/2000 |
| DE | 19948759 A1 | 4/2001 |

(Continued)

OTHER PUBLICATIONS

International Search Report for PCT/EP2009/056594, mailed Sep. 7, 2009.

(Continued)

*Primary Examiner* — Katherine M Shi
(74) *Attorney, Agent, or Firm* — Lathrop & Gage LLP

(57) ABSTRACT

The invention relates to a pricking device (1) for taking a blood sample, comprising a movable holding device (5) for pricking means (4), means (12) for driving the movable holding device and a release device (19) for releasing the pricking movement (13) of the pricking means. When the release device has been manually actuated, the movable holding device can be axially moved by a spring force of a drive spring (9) of the drive means (12), and a tensing device (22) for tensing the drive spring. Said tensing device comprises a tensing mechanism (23) comprising means (24) for axially stopping the movable holding device during the tensing of the drive spring and means (25) for working during the tensing of the drive spring enabling said pricking device to be comfortable to use even when being used several times.

9 Claims, 6 Drawing Sheets

(56) References Cited

U.S. PATENT DOCUMENTS

Figure 11:
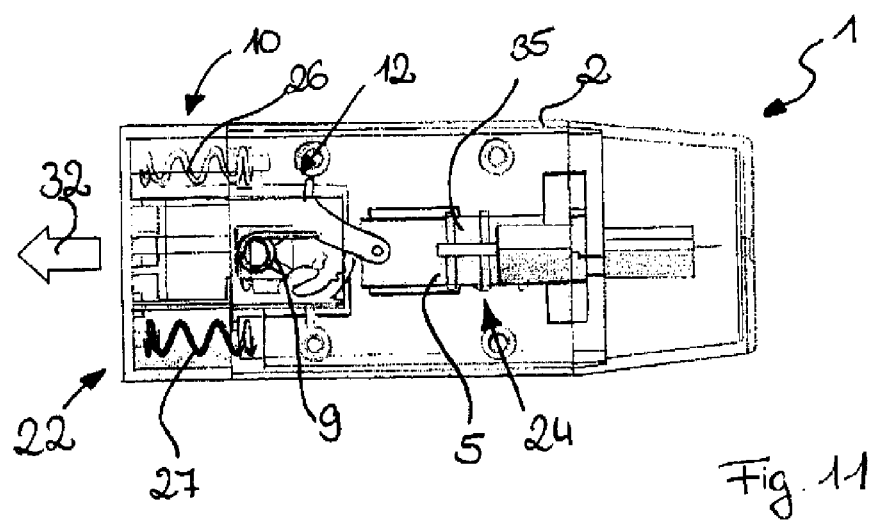

| | | | |
|---|---|---|---|
| 5,527,334 A * | 6/1996 | Kanner et al. ................ | 606/182 |
| 5,951,582 A | 9/1999 | Thorne et al. | |
| 5,954,738 A | 9/1999 | LeVaughn et al. | |
| 6,221,089 B1 | 4/2001 | Mawhirt | |
| 6,409,740 B1 | 6/2002 | Kuhr et al. | |
| 6,419,661 B1 | 7/2002 | Kuhr et al. | |
| 7,842,060 B2 | 11/2010 | List | |
| 2005/0131441 A1 | 6/2005 | Iio et al. | |
| 2005/0145520 A1 | 7/2005 | Ilo et al. | |
| 2006/0155317 A1 | 7/2006 | List | |
| 2010/0168618 A1 | 7/2010 | List | |

FOREIGN PATENT DOCUMENTS

| | | |
|---|---|---|
| EP | 0898936 A2 | 3/1999 |
| EP | 1090584 A2 | 4/2001 |
| EP | 1669028 A1 | 6/2006 |
| WO | 2005/077275 A1 | 8/2005 |

OTHER PUBLICATIONS

International Search Report for PCT/EP2009/056597, mailed Sep. 7, 2009.

Examination Report for European Patent Application No. 09 757 464.4, mailed Mar. 14, 2012, 3 pages.

English translation of the Written Opinion of the International Searching Authority issued Dec. 6, 2010, for International Application No. PCT/EP2009/056597, 5 pages.

Russian Office Action dated Dec. 14, 2012, from the Russian Agency for Industrial Property for Russian Patent Application No. 2010153804/14.

English translation of Russian Office Action dated Dec. 14, 2012, from the Russian Agency for Industrial Property for Russian Patent Application No. 2010153804/14.

Notification of the First Office Action dated Aug. 3, 2012, from the State Intellectual Property Office of China for Chinese Patent Application No. 200980121996.9.

* cited by examiner

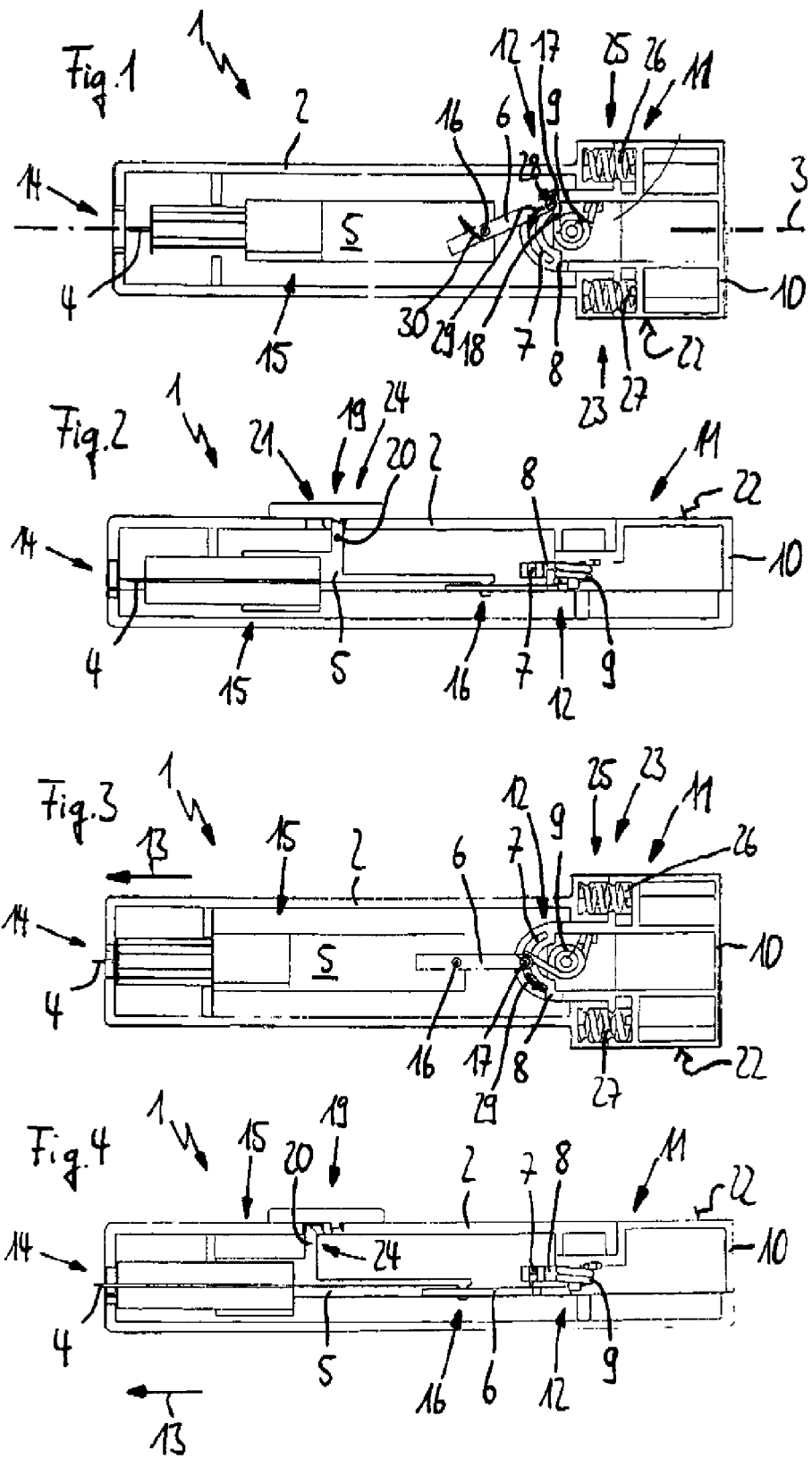

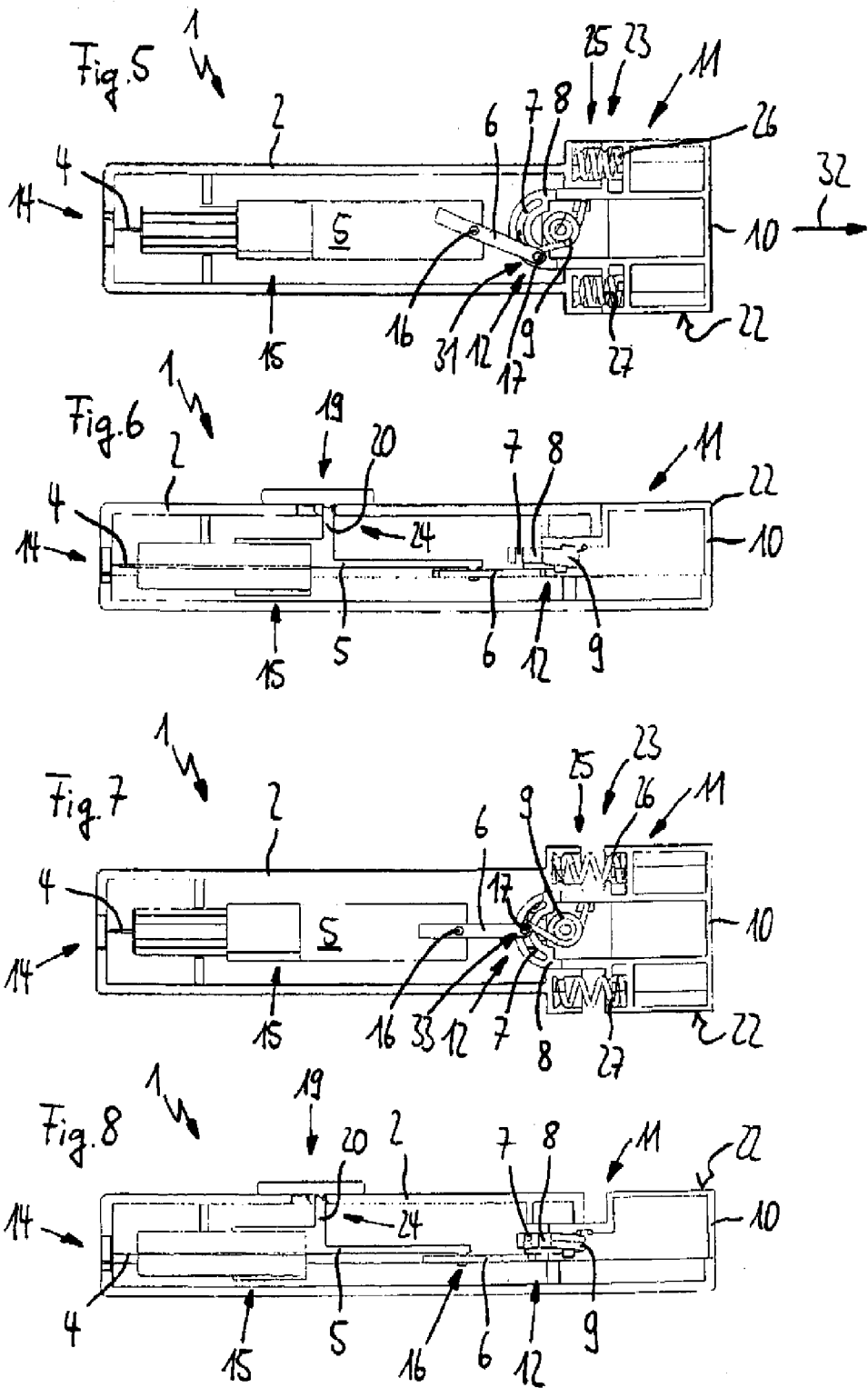

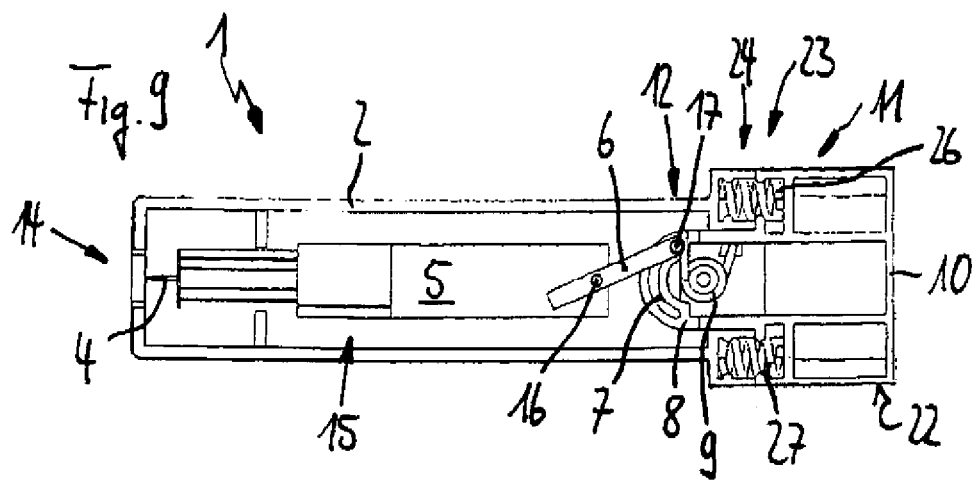
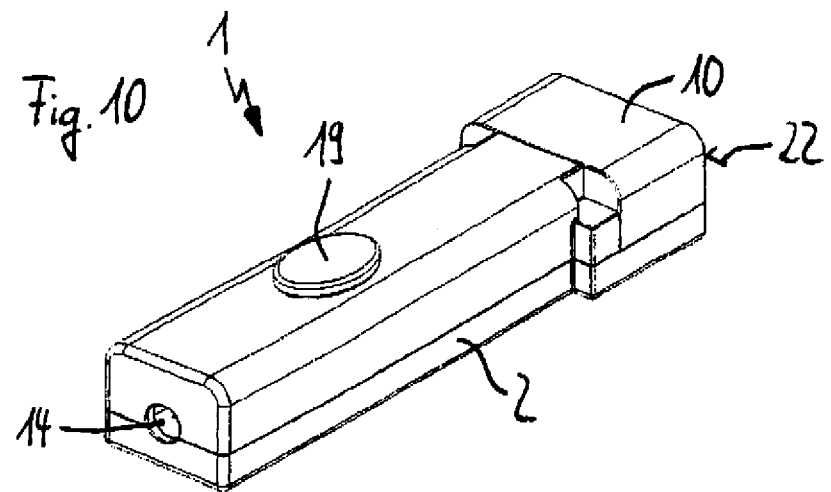

PRICKING DEVICE FOR TAKING A BLOOD SAMPLE

CROSS-REFERENCE TO RELATED APPLICATIONS

This application is a U.S. National Stage Application under 35 U.S.C. §371 of International Application No. PCT/EP2009/056597, filed May 29, 2009, which claims the benefit of German Application No. 102008027272.8, filed Jun. 6, 2008 and German Application No. 102008037082.7, filed Aug. 8, 2008. All three of these applications are hereby incorporated by reference in their entireties.

The invention concerns a pricking device for taking a blood sample with a moveable holder device for a pricking means, with means for driving the moveable holder device and with a trigger device to trigger the pricking movement of the pricking means, wherein after manual activation of the trigger device the moveable holder device can be moved axially by means of a spring force of a drive spring of the drive means.

Generic pricking devices are well known from the prior art and have proved useful for taking blood samples, in particular for blood sugar measurement. Often such pricking devices are only intended for single use. In order to be able to use such pricking devices several times however, it is necessary to re-tension drive springs for example within the pricking device for a new pricking process.

The object of the invention is to refine such generic pricking devices so that repeated use is easier to perform.

The object of the invention is achieved by a pricking device for taking blood samples with a moveable holder device for a pricking means, with means for driving a moveable holder device and with a trigger device for triggering a pricking movement of the pricking means, wherein after manual operation of the trigger device the moveable holder device can be moved axially by means of a spring force of a drive spring of the drive means, wherein the pricking device is characterised by a tensioning device for tensioning the drive spring, wherein furthermore the tensioning device has a tensioning mechanism comprising means for axial locking of the moveable holder device during tensioning of the drive spring and comprising means for performing work during tensioning of the drive spring.

Because of the tensioning device with such a tensioning mechanism, it is substantially easier and more reliable to return the pricking device to a tensioned state ready for operation in order to take a further blood sample.

Evidently the tensioning device can be constructed in various ways. In this case it is essential that the tensioning mechanism of the tensioning device firstly comprises means for axial locking of the moveable holder device in order advantageously to suppress an unintentional movement of the holder device during tensioning of the drive spring. As a result in particular the pricking means can be prevented from moving critically out of a housing of the tensioning device without the intention to take a specific blood sample. Secondly it is essential that the tensioning mechanism comprises means for performing work, in order advantageously to be able to support a tensioning process by force, substantially facilitating the tensioning of the drive spring.

As pricking means, structures such as needles can be used which do not have a round cross section but a rectangular cross section or a cutter-like tip.

The term "drive spring" in the sense of the invention describes any structure by means of which essentially a pricking movement of the pricking means can be initiated. For this in particular the moveable holder device must be accelerated, whereby the pricking means can itself form the moveable holder device. A drive spring can be a leaf spring for example of plastic. Or an elastic rubber tensioner can be used in the sense of the present drive spring. However a drive spring made of metal is preferred in the form of a leg spring as this can permanently provide a substantially constant spring force.

A preferred embodiment provides that the tensioning device comprises an axially moveable tensioning slide. By means of the axially moveable tensioning slide, all components essentially involved in particular in a tensioning process of the drive spring can be moved out of a rest position, which the components have assumed after the pricking movement of the pricking means, to a starting position in a targeted and coordinated manner.

If the axially moveable tensioning slide has a slide support for a control curved track element and/or for a drive spring mounting, these components can particularly advantageously be moved manually in relation to further components of the pricking device such that in a constructionally particularly simple way, they can be positioned again according to a state of the pricking device ready for operation. Evidently further components of the pricking device can advantageously be positioned by means of the moveable tensioning slide if this proves advantageous.

Furthermore it is advantageous if the means for performing work comprise spring elements, preferably two coil springs. The means for performing work can in the present case be achieved by any devices which can act supportingly on tensioning the drive springs. Coil springs have proved sufficiently strong and durable with particularly low maintenance, so that the present coil springs can serve extremely well as means for performing work.

A further preferred embodiment provides that the means for performing work can comprise a tensioning head of the tensioning device sprung-mounted on a base body of the pricking device. As described below for the embodiment examples from the enclosed drawing, the means for performing work can advantageously mount a tensioning head on the housing of the pricking device, wherein the means for performing work can also be pre-tensioned by means of axial deflection of the tensioning head such that by these means, ideally the drive spring can be transferred fully into a tensioned state.

In this context it is advantageous if the means for performing work have a working spring force $F_D$ and the drive spring has a drive spring force $F_S$, wherein the working spring force $F_D$ is greater than the drive spring force $F_S$, whereby the drive spring can be tensioned particularly easily.

In order to transfer the drive spring force $F_S$ in particular from one leg of a leg spring as a drive spring to further components of the drive means in a constructionally simple manner with relatively low loss, it is advantageous if the drive means have a coupling element between the moveable holder device and a control curved track element of the drive means. The coupling device is here mounted swivelable on the moveable holder device so that with its end opposite the holder device mounting it can be deflected radially in relation to an axial movement axis of the holder device. So that the coupling element can be guided in a defined arc section, it is furthermore advantageous if the drive means comprise a curved track, preferably an arc-shaped curved track. In particular by means of such a curved track, the end of the coupling element opposite the holder device mounting can be guided in a targeted manner. By means of the arc-shaped curved track a translational forward movement, maximum axial deflection and a translational return movement of the pricking means can be achieved with a particularly simple construction.

If the drive means comprise a control curved track element, the curved track can advantageously be integrated into one of the drive means.

The coupling element can be guided along with the curved track with high precision if a curved track follower is provided which is arranged inside a profile element of the curved track of the drive means. The curved track follower here can be provided in the form of a peg which protrudes into a curved groove on the control curved track element.

One particularly advantageous embodiment provides that the curved track follower has a forward drive by means of which the curved track follower can be moved along the curved track in a first direction. Such a forward drive can be achieved particularly compactly for example by means of the present drive spring.

Cumulatively or alternatively, it is advantageous if the curved track follower has a return drive by means of which the curved track follower can be moved along the curved track in a second direction opposite the first. A suitable reverse drive can be constituted by the existing means for performing work, in particular in the form of coil springs.

Due to the structure of the present pricking device in particular with regard to the cooperation of individual drive means, it can be guaranteed, in particular functionally reliably, that the same puncture depth and movement course of the pricking means are almost always achieved. This advantageously reduces the puncture pain on penetration of the pricking means into the upper skin layer to take a blood sample. In particular by means of the structure of the present drive means, an undesirable reverberation of the pricking means can be prevented, as occurs with the known spring-guided holding systems. Thus the pricking means in the present case advantageously only pricks once.

Further advantages, objectives and features of the present invention are described below with reference to the attached drawing which shows as an example two embodiments of a pricking device with a tensioning device. Components which largely correlate with regard to function in the figures are marked with the same reference numerals, where these components need not be numbered and explained in all figures.

Figure 12:
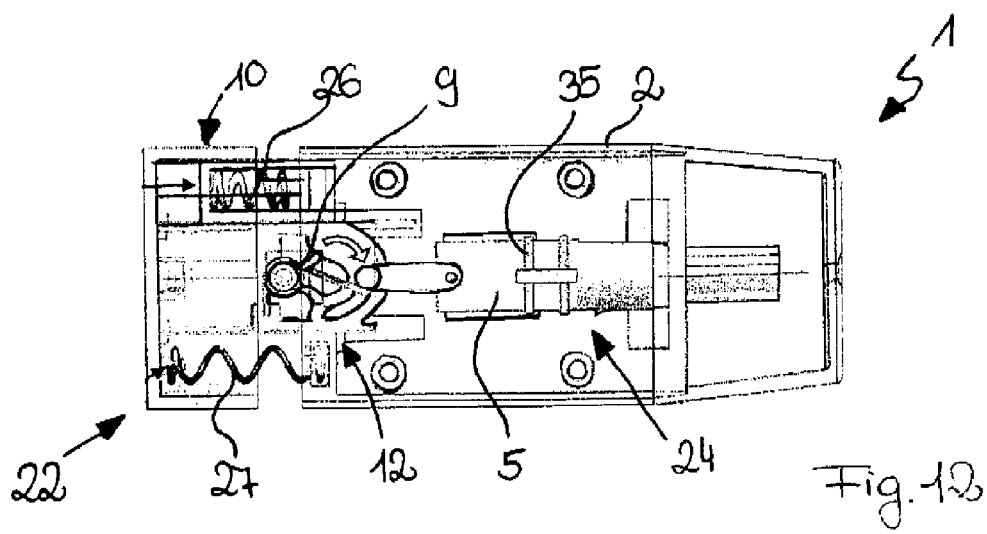
Figure 13:
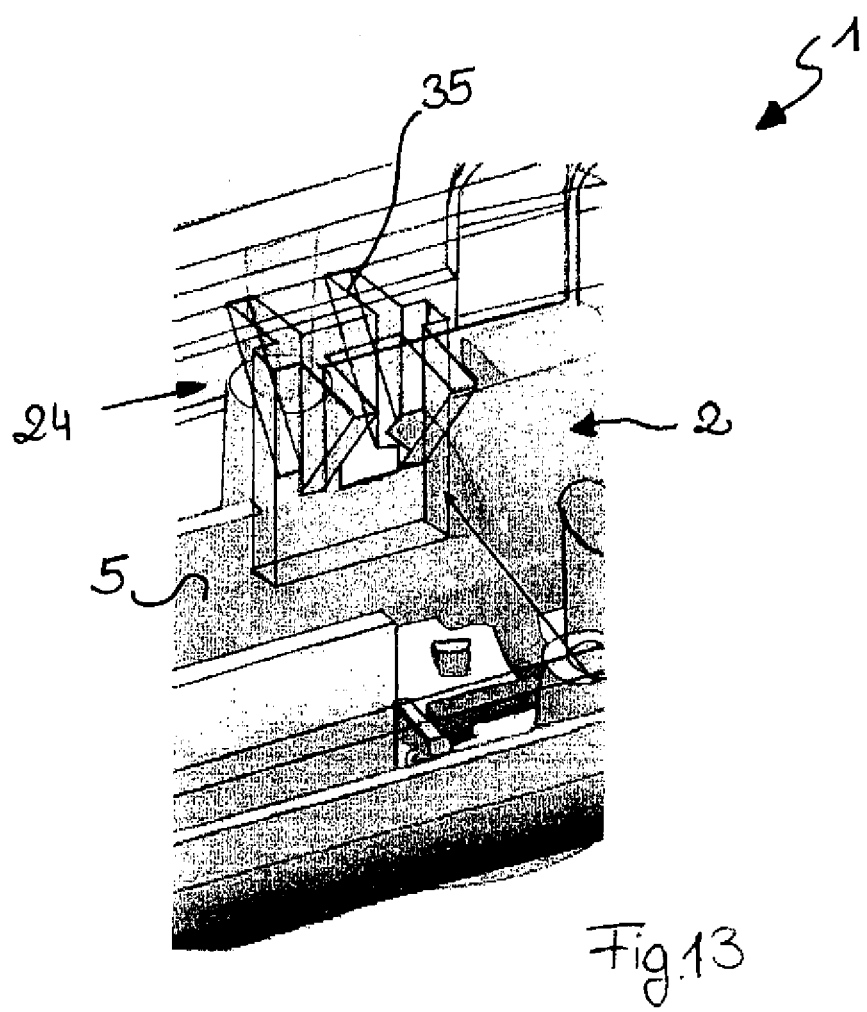
Figure 14:
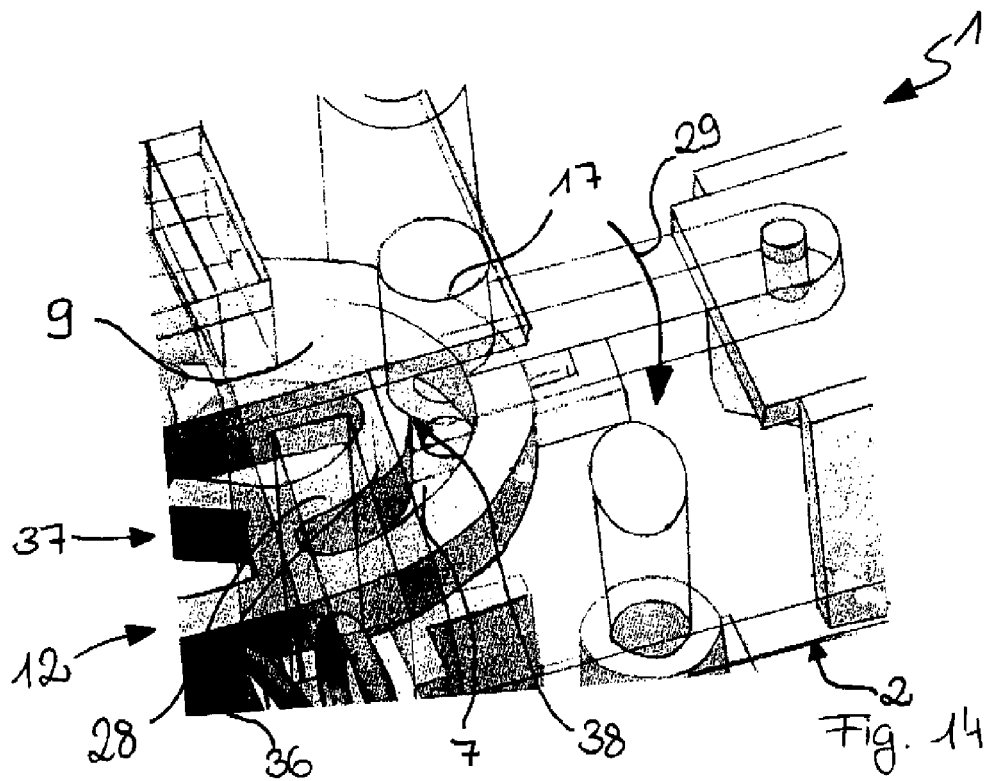
Figure 15:
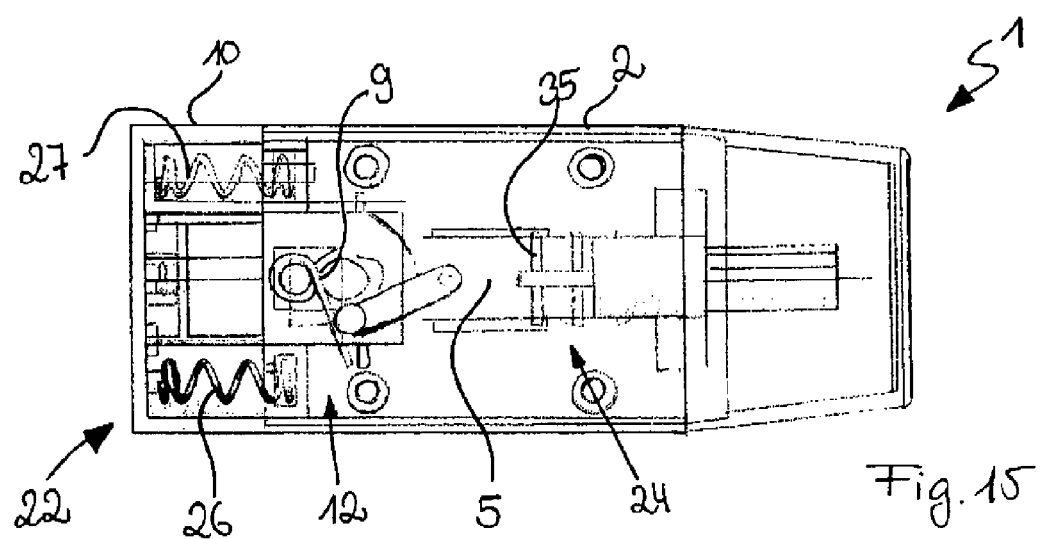

The drawings show:

FIG. 1 diagrammatically a first cross-section view of a first embodiment example of a pricking device in a tensioned state ready for use;

FIG. 2 diagrammatically a further cross-section view of the pricking device of FIG. 1 in a tensioned state ready for use;

FIG. 3 diagrammatically a cross-section view of the pricking device from FIGS. 1 and 2 in a pricking state;

FIG. 4 diagrammatically a further cross-section view of the pricking device from FIGS. 1 to 3 in a pricking state;

FIG. 5 diagrammatically a cross-section view of the pricking device from FIGS. 1 to 4 after a pricking state;

FIG. 6 diagrammatically a further cross-section view of the pricking device from FIGS. 1 to 5 after a pricking state;

FIG. 7 diagrammatically a cross-section view of the pricking device from FIGS. 1 to 6 during a tensioned state;

FIG. 8 diagrammatically a further cross-section view of the pricking device from FIGS. 1 to 7 during a tensioned state;

FIG. 9 diagrammatically a cross-section view of the pricking device from FIGS. 1 to 8 in a re-tensioned state ready for use;

FIG. 10 diagrammatically a perspective view of a housing of the pricking device from FIGS. 1 to 9;

FIG. 11 diagrammatically a view of a second embodiment example of a further pricking device with an axially deflected tensioning head of a tensioning device;

FIG. 12 diagrammatically a view of the further pricking device from FIG. 11 with two different coil spring designs;

FIG. 13 diagrammatically a view relating to means for axial locking of a moveable holding device of a pricking means of the further pricking device from FIGS. 11 and 12;

FIG. 14 diagrammatically a view of an arc-shaped curved track of the further pricking device from FIGS. 11 to 13; and FIG. 15 diagrammatically a view of a working spring tensioned by the means for performing work of the further pricking device from FIGS. 11 to 14.

The pricking device 1 shown in FIGS. 1 to 10 has a housing 2 in which along an axial pricking axis 3 (only drawn and numbered as an example with regard to FIG. 1) are substantially arranged an axially moveable pricking means 4, an axially moveable holder device 5, an axially moveable coupling element 6, an axially moveable arc-shaped curved track 7, an axially moveable control curved track element 8, an axially moveable drive spring 9 and an axially moveable tensioning head 10 with axially moveable tensioning slide 11.

In particular the drive spring 9, the arc-shaped curved track 7, the control curved track element 8 and the coupling element 9 form components of means 12 for driving the axially moveable holder device 5, by means of which the pricking means 4 can perform a translational pricking movement 13 (see FIGS. 3 and 4) through an opening 14 in housing 2.

The axially moveable holder device 5 is mounted linearly moveable in the direction of the axial pricking axis 3 by means of a linear guide 15.

The coupling element 6 is mounted by means of a mounting 16 on the holder device 5 radially swivelable on the moveable holder device 5, wherein the coupling element 6 has a curved track follower 17 in the form of a peg which is in turn mounted moveable inside a suitable profile element (unnumbered here) of the arc-shaped curved track 7.

Thus in particular by means of the drive means 12, an essentially radial movement of a first leg 18 (which for the sake of clarity is numbered in FIG. 1 only) of the drive spring 9 can be translated into an essentially linear movement in particular of the holder device 5.

On the housing 2 of the pricking device 1 is also provided a trigger device 19, by means of which the pricking movement 13 at the pricking device 1 can be triggered. By activating the trigger device 19, a locking device 20 of the moveable holder device 5 can be moved out of its locked position 21 (see FIG. 2), whereby the holder device 5 can be moved translationally in particular according to the pricking movement 13.

The pricking device 1 has also a tensioning element 22 for tensioning the drive spring 9, wherein the tensioning device 22 has a tensioning mechanism 23 to which can be allocated firstly means 24 for axial locking of the moveable holder device 5 during tensioning of the drive spring 9, and secondly means 25 for performing work during tensioning of the drive spring 9.

The locking means 24 in this embodiment example are formed particularly constructionally simply directly by the locking device 20 and corresponding components of the trigger device 19 on the pricking device 1. Evidently such locking means 24 can also be provided on other components of the pricking device 1.

The means 25 for performing work are here formed by a first coil spring 26 and a second coil spring 27. Via the coil springs 26 and 27, the tensioning head 10 of the tensioning device 22 is sprung-mounted on the housing 2 of the pricking device 1.

According to the views in FIGS. 1 and 2, the pricking device 1 is in a tensioned state ready for operation. In this state the curved track follower 17 is positioned in a starting position 28 on an arc-shaped curved track 7. As soon as the trigger device 19 is activated, the locking device 20 is released. As a result a radial movement 29 of the curved track follower 17 can take place along the arc-shaped curved track 7, whereupon the coupling element 6 performs a swivel movement 30.

By the radial movement 29 of the curved track follower 17 along the arc-shaped curved track 7, the coupling element 6 is also moved axially whereby the holder device 5 and the pricking means 4 perform the pricking movement 13.

As shown in the views in FIGS. 3 and 4, the pricking device 1 is then in a pricking state. In this pricking state the pricking means 4 has emerged from the opening 14 of the housing 2 and the curved track follower 17 is in the middle of the arc-shaped curved track 7 facing the opening 14. Under the continued pressurisation of the curved track follower 17 by the first leg 18 of the drive spring 9, a further radial movement 29 of the curved track follower 17 takes place (see FIG. 3).

When the curved track follower 17 according to the depictions in FIGS. 5 and 6 has moved to an end position 31, the pricking means 4 is again retracted into the housing 2. The pricking process is then ended. FIGS. 5 and 6 show the rest state or untensioned state of the pricking device 1. In this untensioned state the curved track follower 17 has reached the other end of the arc-shaped curved track 7 and the drive spring 9 is stretched to a maximum and as a result essentially untensioned.

In order to re-tension the drive spring 9, the tensioning head 10 is deflected axially in the direction of a tensioning movement 32 (see FIG. 5) whereby the arrangement of the drive means 12 is drawn into an extended state (see FIGS. 7 and 8). The curved track follower 17 is now in a middle position 33 in the centre of the arc-shaped curved track 7. At the latest in this extended state, the moveable holder device 5 is fixed axially again by means of the locking means 24.

When the tensioning head 10 is released, by means of the tension force 34 the coil springs 26 and 27 it is drawn against the housing 2, whereby in particular the arc-shaped curved track 7 is moved towards the coupling element 6. As a result the coupling element 6 deflects radially further and the curved track follower 17 can be moved back into the starting position 28 (see FIG. 9). In order for the coil springs 26 and 27 to be able to tension the drive spring 9 in this way, the tension 34 is ideally selected greater than the drive force of the drive spring 9.

According to the view in FIG. 9, the tension head 10 is again in the retracted state in the housing 2 of the pricking device 1. The pricking device 1 is again in the tensioned state ready for operation, as described with regard to FIGS. 1 and 2. Thus a new pricking process can take place.

Further details of such a tension device 22 are shown in FIGS. 11 to 15 for a second embodiment example of a further pricking device 1.

The pricking device 1 of the second embodiment example has a housing 2. On the head side is provided a tension head 10 by means of which means 12 for driving a moveable holding device 5, in particular a drive spring 9 of drive means 12, can be tensioned. For this on the tension head 10 are provided two coil springs 26 and 27 with which the tension head 10 is sprung-mounted on the housing 2. When the tension head 10 is moved in a tension movement 32 away from the housing 2, firstly the coil springs 26 and 27 are expanded and secondly the drive means 12 with holder device 5 are extended in that these components are moved in the direction of the tension movement 32.

With regard to FIG. 12, diagrammatically two different spring designs are shown which can be achieved for the tension head 10 on the pricking device 1. According to one embodiment the coil spring 26 is here formed for example as a compression spring. The coil spring 27 in a second embodiment is formed as a tension spring. The coil spring 27 is permanently attached at the end. Where applicable a tension force and tension travel of the tension head 10 can be set in this way.

In particular according to the view in FIG. 13, alternative means 24 are shown for axial locking of the moveable holder device 5 which are attached radially to the moveable holder device 5. The axial locking means 24 have locking ribs 35 (numbered as examples only) which can correspond with suitable locking lugs (not shown here) for example of a trigger device of a pricking device 1. By means of the locking ribs 35 in particular an axial movement of the holder device 5 during tensioning of the drive spring 9 by means of the tension head 10 or the coil springs 26, 27 can be blocked.

In the view in FIG. 14 with regard to the arc-shaped track 7, it is evident in relation to a profile element 36 that the profile element 36 has a chamfer 38 radially on one side 37, so that a curved track follower 17 can automatically be moved out of a centre position 33 of the arc-shaped curved track 7 with a radial movement 29 back to the starting position 28 of the curved track follower 17 when the drive spring 9 is re-tensioned by means of coil springs 26 and 27 as described above with regard to the first embodiment example. The chamfer 38 in this case forms an approximately straight linear section at the profile element 36 of the arc-shaped curved track 7 so that the curved track follower 17, during tensioning of the drive spring 9, is always deflected onto the correct side 37 of the arc-shaped curved track 7 at which the curved track follower 17 can be positioned in the starting position 28. The side 27 of the arc-shaped curved track 7 offers little resistance to the curved track follower 17 in the area of the chamfer 38 so that the curved track follower 17, from its stopped position, is always moved first along the chamfer 38.

All features disclosed in the application documents are claimed as essential to the invention provided they where novel individually or in combination with respect to the prior art.

LIST OF REFERENCE NUMERALS

1. Pricking device
2. Housing
3. Axial pricking axis
4. Pricking means
5. Moveable holder device
6. Coupling element
7. Arc-shaped curved track
8. Control curved track element
9. Drive spring
10. Tension head
11. Tension slide
12. Means for driving the moveable holder device
13. Pricking movement
14. Opening
15. Linear guide
16. Mounting
17. Curved track follower
18. First leg
19. Trigger device 20. Locking device
21. Locking position
22. Tensioning device
23. Tensioning mechanism
24. Means for axial locking of the moveable holding device
25. Means for performing work
26. First coil spring
27. Second coil spring
28. Starting position
29. Radial movement
30. Swivel movement
31. End position
32. Tensioning movement
33. Centre position
34. Tension force
35. Locking ribs
36. Profile element
37. Side
38. Chamfer

The invention claimed is:

1. A pricking device (1) for taking a blood sample, comprising:
   a moveable holder device (5) for a needle (4);
   a drive means (12) comprising a drive spring (9) for driving the moveable holder device (5);
   a trigger device (19) for triggering a pricking movement (13) of the needle (4), wherein after manual activation of the trigger device (19) the moveable holder device (5) can be moved axially by means of a spring force of the drive spring (9); and
   a tensioning device (22) for tensioning the drive spring (9), wherein the tensioning device (22) comprises:
      a tensioning mechanism (23) comprising a locking device (20) for axial locking of the moveable holder holding device (5) during tensioning of the drive spring (9); and
      spring elements (25) for performing work during tensioning of the drive spring (9);
      wherein the tensioning mechanism (23) comprises an axially moveable tensioning slide (11), wherein the axially moveable tensioning slide (11) has a sliding support and an arc-shaped curved track (7) that guides the moveable holder device (5) in a targeted manner;
   wherein the drive spring (9) is coupled to the sliding support and the arc-shaped curved track (7);
   wherein a coupling element (6) connects the arc-shaped curved track (7) and the moveable holder device (5); and
   wherein a curved track follower (17) is mounted moveable inside a profile element of the arc-shaped curved track (7), such that the curved track follower (17) is configured to move radially along the arc-shaped curve track (7) upon activation of the trigger device (19).

2. Pricking device (1) according to claim 1, characterized in that the axially moveable tensioning slide (11) has a drive spring mounting.

3. Pricking device (1) according to claim 1, characterized in that the spring elements (25) for performing work comprise two coil springs (26, 27).

4. Pricking device (1) according to claim 1, characterized in that the spring elements (25) for performing work are bearing a tensioning head (10) of the tensioning device (22) sprung-mounted on a base body (2) of the pricking device (1).

5. Pricking device (1) according to claim 1, characterized in that the spring elements (25) for performing work have a working spring force $F_D$ and the drive spring (9) has a drive spring force $F_s$, wherein the working spring force $F_D$ is greater than the drive spring force $F_s$.

6. Pricking device (1) according to claim 1, characterized in that the curved track follower (17) has a forward drive by means of which the curved track follower (17) can be moved along the arc-shaped curved track in a first direction.

7. Pricking device (1) according to claim 1, characterized in that the curved track follower (17) has a reverse drive by means of which the curved track follower (17) can be moved along the arc-shaped curved track along in a second direction opposite the first direction.

8. A pricking device (1) for taking a blood sample, comprising:
   a moveable holder device (5) for a needle (4);
   a drive means (12) comprising a torsional drive spring (9) for driving the moveable holder device (5) axially;
   an arc-shaped curved track (7) that guides the moveable holder device (5) in a targeted manner, wherein a coupling element (6) connects the arc-shaped curved track (7) and the moveable holder device (5);
   a curved track follower mounted moveable inside a profile element of the arc-shaped track, such that the curved track follower is configured to move radially along the arc-shaped curve track upon activation of a trigger device; and
   a tensioning device (22) for tensioning the torsional drive spring (9) comprising an axially moveable tensioning slide (11) attached to the arc-shaped curved track (7), wherein the torsional drive spring (9) is coupled to the tensioning slide (11) and the arc-shaped curved track (7), wherein the tensioning device (22) comprises at least one coil spring element (25) for performing work during tensioning of the torsional drive spring (9).

9. The pricking device (1) according to claim 8, wherein the at least one coil spring (25) comprises two coil springs (26, 27).

* * * * *